United States Patent
Wang et al.

(10) Patent No.: US 10,647,979 B2
(45) Date of Patent: May 12, 2020

(54) NUCLEIC ACID EXTRACTION APPARATUS AND METHOD OF OPERATION

(71) Applicant: SHENZHEN MINDRAY BIO-MEDICAL ELECTRONICS CO., LTD., Shenzhen (CN)

(72) Inventors: Hai Wang, Shenzhen (CN); Yanwen Weng, Shenzhen (CN); Yanning Leng, Shenzhen (CN); Chuanfen Xie, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 408 days.

(21) Appl. No.: 15/374,863

(22) Filed: Dec. 9, 2016

(65) Prior Publication Data

US 2017/0088831 A1    Mar. 30, 2017

Related U.S. Application Data

(63) Continuation of application No. PCT/CN2014/080130, filed on Jun. 17, 2014.

(51) Int. Cl.
| | | |
|---|---|---|
| *C12N 15/10* | (2006.01) | |
| *C12Q 1/6848* | (2018.01) | |
| *G01N 35/00* | (2006.01) | |
| *G01N 35/02* | (2006.01) | |
| *G01N 35/04* | (2006.01) | |
| *G01N 35/10* | (2006.01) | |

(52) U.S. Cl.
CPC ....... *C12N 15/1006* (2013.01); *C12Q 1/6848* (2013.01); *G01N 35/0092* (2013.01); *G01N 35/025* (2013.01); *G01N 35/04* (2013.01); *G01N 35/1002* (2013.01); *G01N 2035/00534* (2013.01); *G01N 2035/00564* (2013.01); *G01N 2035/0437* (2013.01); *G01N 2035/0444* (2013.01)

(58) Field of Classification Search
None
See application file for complete search history.

(56) References Cited

U.S. PATENT DOCUMENTS

| | | | | |
|---|---|---|---|---|
| 5,114,858 A | * | 5/1992 | Williams | ............... C12M 47/06 422/527 |
| 6,815,215 B2 | | 11/2004 | Igarashi et al. | |
| 2005/0045533 A1 | | 3/2005 | Fujimoto et al. | |
| 2005/0191760 A1 | * | 9/2005 | Heath | ................ C12N 15/1006 436/177 |

(Continued)

FOREIGN PATENT DOCUMENTS

| | | |
|---|---|---|
| CN | 102539800 A | 7/2012 |
| CN | 102549140 A | 7/2012 |
| CN | 103175977 A | 6/2013 |

*Primary Examiner* — Samuel C Woolwine
(74) *Attorney, Agent, or Firm* — Kory D. Christensen

(57) ABSTRACT

Provided are nucleic acid extraction apparatuses and operation methods thereof. The apparatus may include at least one cyclically moveable annular structure, at least one pipetting mechanism, at least one injection mechanism and a driving mechanism. The annular structure may be provided with a plurality of cuvette positions and a plurality of operation positions. The pipetting mechanism and the injection operation may be arranged along the annular structure. The driving mechanism may drive the annular structure to move cyclically.

18 Claims, 4 Drawing Sheets

(56) References Cited

U.S. PATENT DOCUMENTS

2006/0081539 A1\* 4/2006 Safar .................... B01L 3/5082
  210/695
2010/0075430 A1\* 3/2010 Hofstadler ......... G01N 35/0098
  436/94

\* cited by examiner

NUCLEIC ACID EXTRACTION APPARATUS AND METHOD OF OPERATION

TECHNICAL FIELD

The present disclosure relates to nucleic acid extraction and more specifically to a nucleic acid extraction apparatus and method.

BACKGROUND

Nucleic acid is a basic object of research in molecular biology, and nucleic acid extraction is an important and basic step in molecular diagnostics. There are many methods for extracting DNA or RNA from a biological sample, such as the traditional organic solvent extraction method, silica gel mold column adsorption method, magnetic bead separation method, charge method, and the like. The magnetic bead separation method is the one most widely used and most suitable for automation. In the magnetic bead separation method, the surfaces of small particles containing magnetic materials are processed so that they can adsorb a desired substance, and then the magnetic beads are adsorbed and enriched by magnet, a waste liquid is discarded. The enriched magnetic beads are washed in order to further remove the impurities and other unwanted substances, while the biological substance of interest can be retained due to its adsorption on the magnetic beads. Finally, the biological substance enriched on the magnetic beads is released into a desired solution system under certain conditions.

The existing automated nucleic acid extraction apparatus using the magnetic bead separation method has evolved from an automatic enzyme immunoassay analyzer and is generally referred to as a "plate-type" scheme. In this scheme, a typical 96-well plate or modification plate thereof (collectively referred to as "96-well plate" hereinafter) is used as a processing unit, and the reagent and the sample solution are added through a plurality of parallel pipetting tips, after which shock mixing is performed on the whole plate. After incubation is completed, the plate is sent to a magnetic separation position where magnetic adsorption is performed, and any waste fluid is pipetted by a plurality of parallel pipetting tips. The operations are repeated a certain number of times to clear interfering substances other than nucleic acids. Thereafter, elution processing is performed on the 96-well plate on which the clearing is completed to obtain elution products (i.e., nucleic acids dispersed in the eluent). Finally, the elution products are brought to a new 96-well plate by pipetting tips so as to be mixed with PCR (polymerase chain reaction) reagent in order to be used in nucleic acid detection of the next step or in other nucleic acid detection or processing operations.

Because the PCR detection uses the 96-well plate as the test unit, the nucleic acid extraction apparatus generally also uses the 96-well plate as the test unit in each test step. However, cross contamination may occur sometimes during PCR detection, which, as suggested by studies, is related to the use of the 96-well plate as the test unit in each test step in the nucleic acid extraction apparatus. In this plate-type scheme, a plurality of samples is processed in parallel. Because the well spacing and the well depth are small, the reaction solution is prone to enter into and thereby pollute the surrounding wells. Furthermore, the pipetting process and discharging process, which are performed in parallel by a plurality of tips, may likely increase the risk of cross contamination. In addition, the mixing operation performed by shocking the whole plate may also likely cause cross contamination.

Since the exponential increase to the nucleic acid provided by the PCR technology leads to very high test sensitivity and the linear range is very wide, there are very high requirements for cross contamination in the PCR technology. However, the plate-type scheme has important defects as mentioned above in avoiding cross contamination, which is an important factor limiting the application of this scheme in clinical practice. Therefore, nucleic acid extraction apparatuses which can prevent cross contamination are needed.

SUMMARY

Nucleic acid extraction apparatuses and methods of operation thereof are provided.

DETAILED DESCRIPTION

Figure 1:
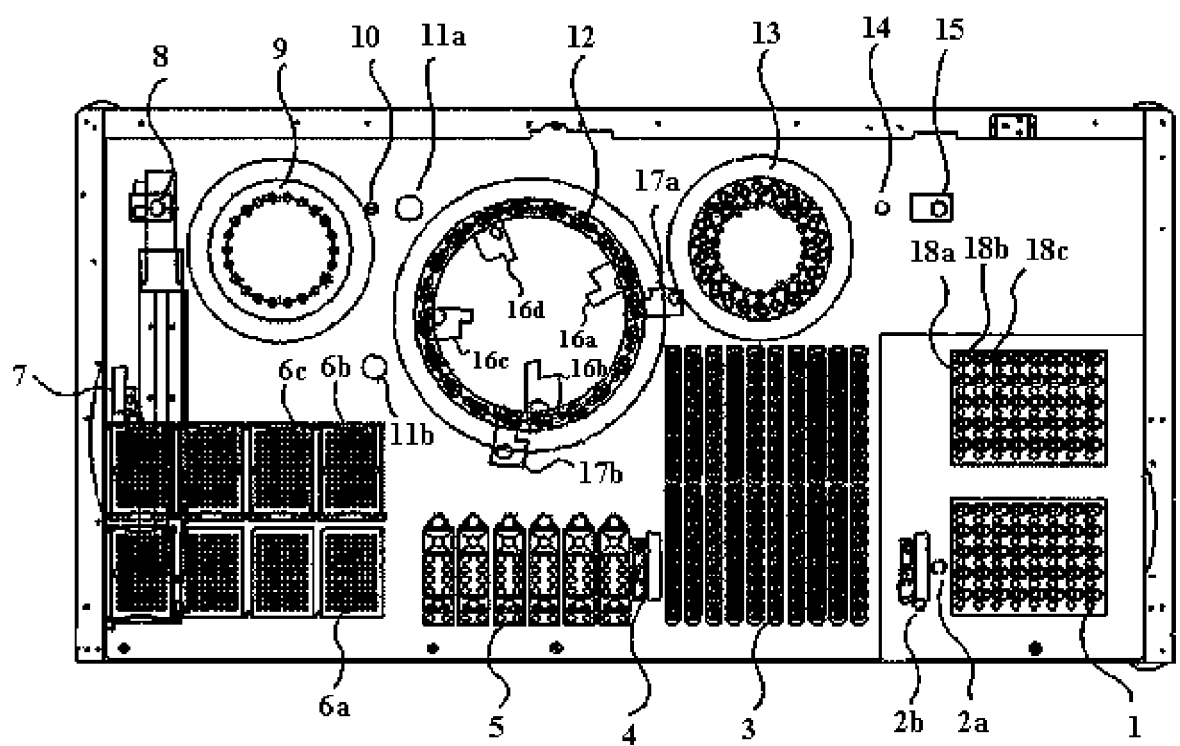
FIG. 1 is a schematic top view of a nucleic acid extraction apparatus according to an embodiment of the present disclosure.

In some embodiments of the present disclosure, a nucleic acid extraction apparatus is provided, which may include at least one cyclically moveable annular structure, at least one pipetting mechanism, at least one injection mechanism and a driving mechanism.

The annular structure may be provided with a plurality of cuvette positions which are arranged at intervals and used for carrying reaction vessels. The annular structure may be provided, along a cyclical movement path thereof, with at least one operation position used for performing a pipetting operation and at least one operation position used for performing an injection operation.

The at least one pipetting mechanism may perform the pipetting operation and may be arranged along the annular structure, the at least one injection mechanism may perform the injection operation and be arranged along the annular structure, and the driving mechanism may drive the annular structure to move cyclically.

In some embodiments of the present disclosure, a nucleic acid extraction apparatus may include an incubation mechanism, a separation mechanism, at least one pipetting mechanism, at least one injection mechanism, and at least one transport mechanism.

The incubation mechanism may provide an incubation place for reaction solutions.

The separation mechanism may separate nucleic acid-binding carrier adsorbed with nucleic acid from the reaction solutions. The separation mechanism may be a cyclically moveable annular structure and may be provided, along an annulus thereof and at intervals, with a plurality of cuvette positions which are arranged in at least one column and used for carrying reaction vessels. The separation mechanism may be provided, along a cyclical movement path thereof, with (i) an in/out position used for taking the reaction vessels out of the separation mechanism or inserting the reaction vessels into the separation mechanism, (ii) at least one pipetting position and (iii) at least one injection position.

The at least one pipetting mechanism may perform a pipetting operation at the pipetting position of the separation mechanism, the at least one injection mechanism may perform an injection operation at the injection position of the separation mechanism, and the at least one transport mechanism may transport the reaction vessels in and out of the various mechanisms.

In some embodiments of the present disclosure, an operation method of the nucleic acid extraction apparatus described above may include: driving the annular structure to cause the reaction vessels to cyclically step at a predetermined rotation step length and in a predetermined rotation direction, and performing a predetermined operation during a stop period; when the annular structure stops for performing operations at the at least one pipetting mechanism and the at least one injection mechanism, performing predetermined operations on the reaction vessels located on the operation positions; and when the predetermined operations are completed, the reaction vessels continuing to be transported to the next operation position within the annular structure.

In some embodiments of the present disclosure, an operation method of the nucleic acid extraction apparatus described above may include: driving the separation mechanism to cyclically step at a predetermined rotation step length and in a predetermined rotation direction, and performing a predetermined operation during a stop period; and, when the separation mechanism stops for performing operations, the transport mechanism picking up the reaction vessels on which the incubation is completed from the incubation mechanism to the in/out position of the separation mechanism, or picking up the reaction vessels on which the separation is completed and which are located in the in/out position of the separation mechanism.

In the nucleic acid extraction apparatus according to the present disclosure, a cyclically moveable annular structure may be used, on which the pipetting and injection operations may be performed, and the cuvette positions may be arranged at intervals such that, when the nucleic acid extraction is performed, a single reaction vessel may be used as a processing unit and processed one by one. Thereby the distance between the tests may be increased and the parallel operations between different tests may be reduced, and thus the cross contamination problem between the tests may be effectively solved.

The present disclosure will be further described in detail by reference to specific embodiments and the corresponding drawings.

A nucleic acid extraction apparatus according to an embodiment of the present disclosure may be used to achieve full automation of nucleic acid extraction—i.e., the apparatus may automatically implement all of the test steps (e.g., reaction solution injection, mixing and incubation, magnetic separation, and elution) involved in the nucleic acid extraction process. The nucleic acid extraction apparatus may include at least one cyclically moveable annular structure, at least one pipetting mechanism which may perform the pipetting operation and be arranged along the annular structure, at least one injection mechanism which may perform the injection operation and be arranged along the annular structure, and a drive mechanism which may drive the reaction vessels located on the annular structure to move them along the cyclical movement path of the annular structure. The annular structure may be provided with a plurality of cuvette positions spaced at intervals and used for carrying reaction vessels, and may be provided, along the cyclical movement path thereof, with a plurality of operation positions used for performing pipetting operations or injection operations. In the present embodiment, the annular structure may comprise structures which are connected in series and are cyclically moveable, and its shape is not limited. For example, the annular structure may be a circular track, a square track, or serpentine track.

In an embodiment, the fluids which can be injected by the injection mechanism may include a sample, a reagent, a nucleic acid-binding carrier, a washing fluid and an eluent. The injected fluid may be related to the corresponding operation. For example, in the separation operation, the injected fluid may be the washing fluid. In an example, during the incubation operation, the injection of the nucleic acid-binding carrier may be performed by other injection mechanisms which are not arranged along the annular structure but are arranged in the vicinity thereof. In another example, during the elution operation, the injection of the eluent may be performed, not by the injection mechanisms arranged along the annular structure, but instead by other injection mechanisms additionally arranged in the vicinity of the annular structure. In addition, after the separation operation is performed, a detection reagent may be directly injected to perform the detection.

In one embodiment, there may be only one annular structure. That is, the annular structure may integrate the incubation operation, the separation operation, and the elution operation. These operations may be similar to those involved in existing nucleic acid extraction processes. For example, the incubation operation may include incubating the reaction solution, the separation operation may include separating the nucleic acid-binding carrier adsorbed with nucleic acid from the incubated reaction solution, and the elution operation may include adding eluent into the reaction vessels after separation to form the elution products. The elution products may or may not include the nucleic acid-binding carrier.

In another embodiment, there may be two annular structures—i.e., a first annular structure and a second annular structure. The first annular structure may be used to perform any two of the incubation operation, the separation operation and the elution operation, and the second annular structure may be used to perform the remaining one operation.

In another embodiment, there may be three annular structures, of which one may be used to perform the incubation operation, another may be used to perform the separation operation, and the remaining one may be used to perform the elution operation.

In order to further solve the cross contamination problem caused by the injection needle during the nucleic acid extraction, the pipetting mechanism may perform the pipetting operation using disposable pipetting tips. It will be understood that the nucleic acid extraction apparatus may be further provided with at least one transport mechanism used to transport the reaction vessels in and out of the annular structure. Furthermore, during the nucleic acid extraction, the reaction solutions in the reaction vessels often need to be mixed. Therefore, the nucleic acid extraction apparatus may be further provided with at least one mixer in order to mix the reaction solutions in the reaction vessels.

In one embodiment, before the nucleic acid extraction apparatus performs the elution operation, during the stop period of the transport of the reaction vessels by the transport mechanism, the transport mechanism may further transport the circulation tubes which follow the reaction vessels and are used to carry and receive the waste fluid. The circulation tubes may further carry the pipetting tips. The circulation tubes may be used cooperatively with the reaction vessels, and thereby the cross contamination caused by the injection or the pipetting is further avoided. The annular structure may be provided with circulation tube positions which may be adjacent to the cuvette positions.

In the nucleic acid extraction apparatuses of the present embodiment, the cuvette positions carrying the reaction vessels may be arranged on the cyclically moveable annular structure at intervals, and operations such as pipetting, injection and the like may all be performed on the annular structure. Specifically, the annular structure may be driven to cause the reaction vessels to cyclically step forward at a predetermined rotation step length and in a predetermined rotation direction, and the predetermined operation may be performed during the stop period. When the annular structure stops for performing the operation, the at least one pipetting mechanism and the at least one injection mechanism may perform the predetermined operation on the reaction vessels located on the operation positions. After the predetermined operation is completed, the reaction vessels may continue to be transported within the annular structure. Therefore, unlike in the traditional plate-type structure in which using the whole plate as the processing unit will lead to cross contamination, when the nucleic acid extraction apparatus of the present embodiment performs the nucleic acid extraction, a single reaction vessel may be used as the processing unit, and the processes may be performed one by one. In this scheme, the distance between the tests can be increased, and the parallel operation between different tests can be reduced, and thereby the cross contamination problem between the tests can be effectively solved.

Yet another embodiment takes the case of three annular structures as an example. Other cases with other numbers of annular structures may be similar to the embodiment described below. In this embodiment, a nucleic acid extraction apparatus may include an incubation mechanism, a separation mechanism, an elution mechanism, a pipetting mechanism, an injection mechanism, and at least one transport mechanism used for transporting the reaction vessels in and out of the various mechanisms. It will be understood that, in this embodiment, the nucleic acid extraction and the detection are separated, and the nucleic acid extraction is described according to three test steps: incubation, separation and elution. In another example, elution may not be performed during nucleic acid extraction. Rather, after the incubation operation and the separation operation, the detection reagent may be directly injected to perform the detection.

The incubation mechanism may be used to provide an incubation place for the reaction solutions, and may comprise cyclically moveable annular structures. The annular structures may be provided, along the annulus thereof and at intervals, with a plurality of cuvette positions which are arranged in at least one column and used for carrying the reaction vessels. Furthermore, the incubation mechanism may be provided, along the cyclical movement path thereof, with mixing positions used for taking the reaction vessels out of the incubation mechanism to perform the mixing, insertion positions used for inserting the reaction vessels into the incubation mechanism, sample addition positions and reagent addition positions. In a specific embodiment, the nucleic acid extraction apparatus may further include an incubation mixer, and the injection mechanism may include a sample addition mechanism and a reagent addition mechanism. The incubation mechanism may be cyclically stepped at a predetermined rotation step length and in a predetermined rotation direction. During the stop period of the incubation mechanism for performing the operation, the transport mechanism may pick up the reaction vessels located on the mixing positions of the incubation mechanism to the incubation mixer, or pick up the reaction vessels in the incubation mixer of which the mixing is completed to the mixing positions. The transport mechanism may pick up empty reaction vessels to the inserting positions of the incubation mechanism. The sample addition mechanism may add sample into the reaction vessels located on the sample addition positions of the incubation mechanism. The reagent addition mechanism may add reagent into the reaction vessels located on the reagent addition positions of the incubation mechanism. As in the previous embodiment, in order to further solve the cross contamination problem caused by the injection needle, the incubation mechanism may be further provided, along the annulus thereof, with a plurality of circulation tube positions which are used for carrying the circulation tubes containing the waste fluid and the pipetting tips. The circulation tube position may be adjacent to the cuvette position corresponding thereto. During the stop period of the transporting of the reaction vessels, the transport mechanism may further transport the circulation tubes following the reaction vessels.

The separation mechanism may be used to separate the nucleic acid-binding carrier adsorbed with the nucleic acid from the reaction solutions. The separation mechanism may comprise cyclically moveable annular structures, and may be provided, along the annulus thereof and at intervals, with a plurality of cuvette positions which are arranged in at least one column and used for carrying the reaction vessels. The separation mechanism may be provided, along the cyclical movement path thereof, with in/out positions used for taking or inserting the reaction vessels out of or into the separation mechanism, at least one pipetting position and at least one injection position. The separation mechanism may be cyclically stepped at a predetermined rotation step length and in a predetermined rotation direction and may perform the predetermined operation during the stop period. During the stop period of the separation mechanism for performing the operation, the transport mechanism may pick up the reaction vessels on which the incubation is completed from the incubation mechanism to the in/out positions of the separation mechanism, or pick up the reaction vessels which are located on the in/out positions of the separation mechanism and on which the separation is completed to the elution mechanism. The pipetting mechanism may be used to perform the pipetting operation at the pipetting positions of the separation mechanism. The injection mechanism may include a washing fluid injection mechanism and may be used to perform the injection operation at the injection position. During the stop period of the separation mechanism for performing operations, the pipetting mechanism and the injection mechanism may respectively perform predetermined operations to the reaction vessels stopped at the pipetting position and the injection position. As in the previous embodiment, in order to further solve the cross contamination problem caused by the injection needle, the separation mechanism may be further provided, along the annulus thereof, with a plurality of circulation tube positions which are used for carrying the circulation tubes carrying the waste fluid and the pipetting tips. The circulation tube position may be adjacent to the cuvette position corresponding thereto. During the stop period of the transporting of the reaction vessels, the transport mechanism may further transport the circulation tubes following the reaction vessels.

When, for example, the magnetic separation method is used to extract the nucleic acid, the inner side or outer side of the separation mechanism may further be provided with an adsorption mechanism which provides desired adsorption force for the reaction vessels located at predetermined positions on the separation mechanism.

The elution mechanism may be used to form the elution products by adding eluent, may be cyclically moveable annular structures, and may be provided, along the annulus thereof and at intervals, with a plurality of cuvette positions which are arranged in at least one column and used for carrying the reaction vessels. Furthermore, the elution mechanism may be provided, along the cyclical movement path thereof, with mixing positions, inserting positions used for inserting the reaction vessels into the elution mechanism, and eluent addition positions. In an embodiment, the nucleic acid extraction apparatus may further include a nucleic acid mixer. The injection mechanism may include an eluent addition mechanism. The elution mechanism may be cyclically stepped at a predetermined rotation step length and in a predetermined rotation direction. During the stop period of the elution mechanism for performing operations, the transport mechanism may pick up the reaction vessels located on the mixing positions of the elution mechanism to the nucleic acid mixer, or pick up the reaction vessels in the nucleic acid mixer of which the mixing is completed to the mixing positions. The eluent addition mechanism may add eluent into the reaction vessels located on the eluent addition positions of the elution mechanism.

The foregoing embodiment will be described in detail with reference to the specific structure of the nucleic acid extraction apparatus of an example.

As shown in FIG. 1, the nucleic acid extraction apparatus may include a work bench, on which a plurality of work regions may be arranged. The work regions may include a consumables region 1, a sample region 3, a reagent region, a nucleic acid storage region 6a and a waste recovery region 11a, etc. The work bench may further be provided with a transport mechanism, an incubation mechanism, a separation mechanism 12 and an elution mechanism. The consumables desired during the extraction and test processes of the nucleic acid may be placed on the consumables region 1, including the reaction vessels (such as cuvette 18a), the circulation tube 18b cooperatively used with the cuvette 18a and the pipetting tips 18c. The samples to be detected may be placed on the sample region 3. The kits 5 desired for the experiment may be placed on the reagent region. The kits 5 may carry all of the reagents (such as magnetic bead reagent, eluent and the like) desired for a test item and corresponding reagent pipetting tips. The extracted nucleic acid may be placed on the nucleic acid storage region 6a. The waste fluid generated during the nucleic acid extraction and the used pipetting tips may be collected in the waste recovery region 11a.

When performing the nucleic acid extraction, sample and reagent need to be added to the reaction vessels from the sample region 3 and the reagent region. After the addition, the reaction vessels may be transported to other operation mechanisms. That is, units which provide the sample addition function and reagent addition function are needed. In FIG. 1, a sample addition unit 2b is provided, which may be used to pipette the sample from the sample region 3 and inject the sample into the cuvette 18a. In this case, a consumables grasper 2a and a consumables holding arm (not shown) may be arranged. The consumables grasper 2a may achieve the operation of transporting the cuvette 18a and the circulation tube 18b from the consumables region 1 to other operation mechanisms. The consumables holding arm may achieve the operations of loading the pipetting tip 18c from the consumables region 1 and adding the sample to the reaction vessels from the sample region 3, and unloading the pipetting tip 18c to the circulation tube 18b. In FIG. 1, a reagent addition unit 4 is further provided, which may be used to pipette reagent from the kits 5 in the reagent region and inject the reagent to the cuvette 18a. The reagent addition unit 4 may include a reagent holding arm (not shown), which may achieve the operation of pipetting the reagent from the kits 5 through the reagent pipetting tip and injecting the reagent to the cuvette 18a.

The incubation mechanism may perform the incubation operation on the cuvette 18a in which the sample and the reagent have been added, and transport the cuvette 18a to the corresponding position in the separation mechanism after the mixing is completed. Specifically, in this case, an incubation grasper 14, an incubation plate 13 and an incubation mixer 15 may be provided. The incubation grasper 14 may grasp the cuvette 18a from the incubation plate 13 to the incubation mixer 15 or the separation mechanism, or grasp the cuvette 18a from the incubation mixer 15 to the incubation plate 13. The incubation plate 13 may receive the cuvette 18a and the circulation tube 18b sent by the consumables grasper 2a, and achieve the incubation to the fluid in the cuvette 18a. The incubation mixer 15 may achieve the incubation and mixing operations to the fluid in the cuvette 18a.

Figure 2:
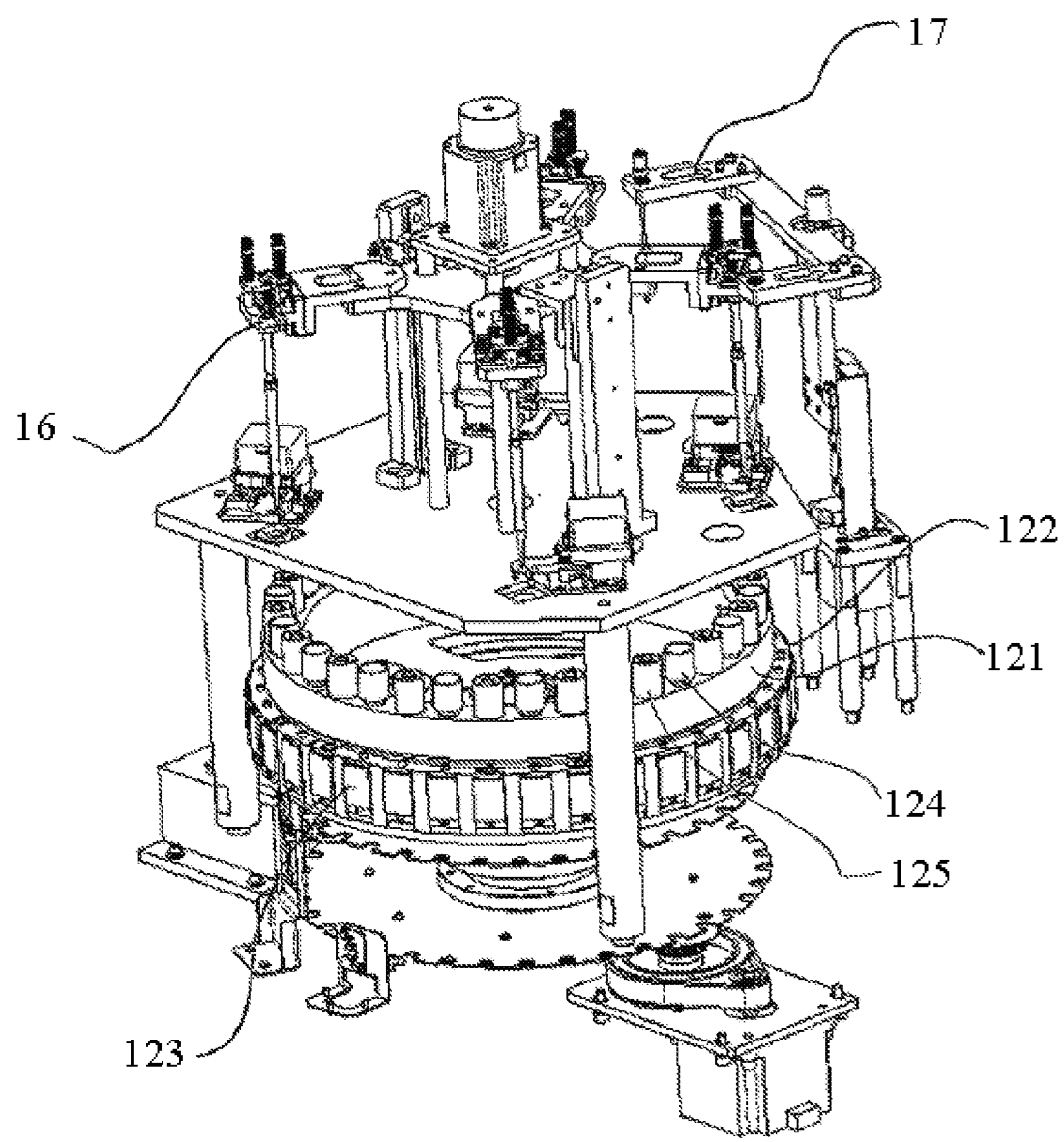
FIG. 2 is a schematic perspective view of the separation mechanism in FIG. 1.

In the present embodiment, a magnetic separation device may be used to remove the interference substances in the reaction vessels. In order to solve the existing cross contamination problem caused by sharing the pipetting tips, a solution of using disposable pipetting tips in the separation mechanism may also be used. In the present embodiment, the separation mechanism may be a circular separation plate. As shown in FIG. 2, the magnetic separation device may include a separation plate 121, an adsorption mechanism 122, pipetting parts 16 (which may correspond to 16a-16d in FIG. 1), injection parts 17 (which may correspond to 17a-17b in FIG. 1) and a moving part (not shown in the figure).

In an embodiment, the separation plate 121 may be a cyclically moveable annular structure. The separation plate 121 may be provided, along the annulus thereof and at intervals, with a plurality of cuvette positions 124 which are arranged in at least one column and used for carrying the reaction vessels, and provided with circulation tube positions 125 used for carrying the circulation tubes cooperatively used with the reaction vessels. Each circulation tube position 125 may be adjacent to the corresponding cuvette position 124. The cyclically moveable annular structure may be provided, along the cyclical movement path thereof, with a plurality of pipetting positions and at least one injection position. In the present embodiment, the adsorption mechanism 122 may be annular and arranged at an outer ring of the separation plate 121. In other embodiments, the adsorption mechanism 122 may also be arranged at an inner ring of the separation plate 121. The adsorption mechanism 122 may provide desired adsorption force for the nucleic acid-binding carrier in the reaction vessels on the separation plate 121, such that the nucleic acid-binding carrier in the reaction vessels may be aggregated to the side of the reaction vessels close to the adsorption mechanism 122. The pipetting parts 16 may be used to perform the pipetting operation at the pipetting positions. The injection parts 17 may be used to perform the injection operation at the injection positions. The moving part may be used to drive the separation plate 121 and the adsorption mechanism 122 to rotate or stop.

In the present embodiment, the adsorption mechanism 122 may be provided, along the annulus thereof, with a plurality of adsorption parts (such as magnets 123) which can adsorb extract-binding carriers. Furthermore, the adsorption mechanism 122 may be provided with at least one vacancy position (not shown in the figure) without adsorption parts. Different operations may have different requirements for the adsorption force of the nucleic acid-binding carrier. Some operations (or time periods) need the adsorption force, while some do not. Therefore, during the rotation or stop period of the reaction vessels, the moving mechanism may drive the vacancy position on the adsorption mechanism without adsorption force to move along with the position where the adsorption force does not need to be provided for the extract-binding carrier. The separation plate 121 and the adsorption mechanism 122 may be independently rotated and stopped under the driving of the moving part, such that the vacancy position of the adsorption mechanism 122 may be synchronously moved along with the cuvette positions on which the reaction vessels needing no adsorption force are located, and thereby, during the period, the nucleic acid-binding carrier in the reaction vessels may not be subjected to the adsorption force and may be suspended in the solutions, which may be favorable to binding more extracts and washing away the impurities on the extract-binding carrier. In a specific example, during the rotation or stop period of the reaction vessels, at least when the washing fluid is added into the reaction vessels on the separation plate 121 and the process is in mixing stage, the moving mechanism may drive the vacancy positions of the adsorption mechanism 122 to move synchronously along with the cuvettes of the reaction vessels such that the extract-binding carriers in the reaction vessels may not be subjected to the adsorption force in the mixing stage after the addition of the washing fluid.

As shown in FIG. 1 and FIG. 2, the separation mechanism may carry the cuvettes 18a on which the magnetic separation needs to be performed and the circulation tubes 18b cooperatively used with the cuvettes 18a. The circulation tubes 18b may be used for carrying the pipetting tips 18c and storing the waste fluid. The pipetting parts 16 and the injection parts 17 may be arranged above the running track of the cuvette 18a. There may be four pipetting parts 16 (16a-16d) and two injection parts 17 (17a-17b). The pipetting parts 16 can pipette the fluid in the cuvette 18a only after the pipetting tips 18c are loaded. A magnetic field ring (i.e., adsorption mechanism 122) may be arranged outside of, and may be rotated concentrically with, the magnetic separation plate 121. Magnets 123 may be mounted on the magnetic field ring at fixed locations and used for adsorbing the magnetic beads in the cuvettes 18a.

Figure 3:
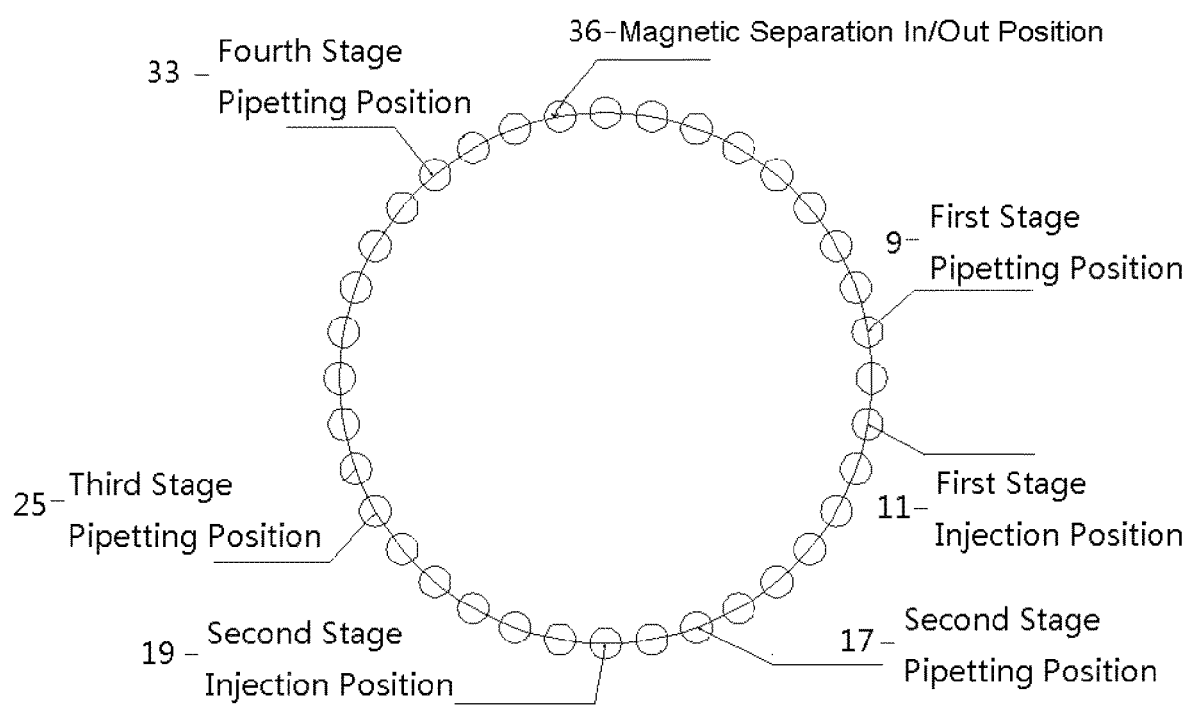
FIG. 3 schematically shows the working process of the separation mechanism shown in FIG. 2.

In a specific embodiment, as shown in FIG. 3, magnetic separation plate 121 may be provided with 36 positions which are evenly arranged and used for carrying the cuvettes and the circulation tubes, respectively. The cuvettes and the circulation tubes may enter into the magnetic separation plate 121 alternately. At the beginning of the work, the cuvette and the circulation tube may be placed in the magnetic plate 121 by an instrument (incubation grasper 14) one after the other from the 36th position on the magnetic separation plate 121. Then, with the rotation step of the magnetic separation plate 121, a magnetic field exists at the outside magnetic field ring location corresponding to the cuvette, such that the magnetic beads may be adsorbed to one side of the cuvette. When the circulation tube is rotated to the 9th position (i.e., below the pipetting mechanism in the first stage) with the magnetic separation plate, the pipetting mechanism may be moved downward to load the pipetting tip in the circulation tube, and then be lifted up. And then, the magnetic separation plate may be moved backward by one position such that the cuvette may just enter the 9th position on the magnetic separation plate, and the pipetting mechanism may be moved downward to pipette the fluid in the cuvette and then be lifted up. Then, the magnetic separation plate may continue to be moved forward by one position such that the circulation tube is located at the 9th position on the magnetic separation plate, and then the pipetting mechanism may be moved downward to discharge the waste fluid and unload the pipetting tip. (During this process, because in the circulation tube the waste fluid discharging position and the pipetting tip unloading position are not consistent, the magnetic separation plate may be moved again to the pipetting tip unloading position after the discharging of the waste fluid is completed; of course, it may also be possible to design the circulation tube such that the two positions are consistent, in which case the movement of the magnetic separation plate may be unnecessary.) At this point, the first stage pipetting action of the magnetic separation may be completed. During the process above, the magnetic separation plate and the magnetic field ring outside thereof may consistently maintain synchronous movement or stop. Therefore, the cuvette may have been in a magnetic adsorption state. After the first stage pipetting action is completed, the magnetic separation plate may continue to be moved forward by three positions such that the cuvette enters the 11th position on the magnetic separation plate (i.e., below the injection mechanism). During the forward movement of the magnetic separation plate, the relative motion between the magnetic field ring and the magnetic separation plate may occur such that the portion on the magnetic field ring without the magnetic field corresponds to the cuvette. At this time, the injection mechanism may inject the washing fluid into the cuvette in the absence of magnetic field adsorption. Then, the magnetic separation plate may be moved backward by three positions such that the circulation tube backs again to the first stage pipetting position. The pipetting mechanism may be moved downward to load the pipetting tip, and then the magnetic separation plate may continue to be moved backward by one position such that the cuvette is located below the first stage pipetting position. The pipetting mechanism may be moved downward to perform the suction mixing on the washing fluid and magnetic beads in the cuvette, and then be lifted up. Then, the magnetic separation plate may continue to be moved forward by one position such that the circulation tube is located below the pipetting mechanism to unload the pipetting tip. At this point, the first stage injection and mixing actions of the magnetic separation are completed. During this process, the magnetic separation plate and the magnetic field ring may have maintained synchronous movement and stop. Therefore the cuvette may have been in a state of non-magnetic field adsorption, which is favorable to the re-suspending of the magnetic beads in the washing fluid. After the mixing is completed, the magnetic field ring may be rotated again relative to the magnetic separation plate such that the cuvette is in a state of magnetic field to perform the magnetic adsorption of the next stage. The pipetting, injection and mixing actions of the magnetic separation of the second stage may be similar to the processes above. Then, in the third stage, only the pipetting action may be performed. The injection action may not be performed and the fluid in the cuvette may be completely pipetted. The fourth stage may be similar to the third stage, in which the injection action may not be performed and only the pipetting action may be performed in order to further pipette the residual liquid at the bottom of the cuvette. At this point, the whole magnetic separation action is completed. Then, the cuvette and the circulation tube may continue to be moved with the magnetic separation plate to back to the 36th position, and may be taken away by an instrument to perform the following operations. Of course, this process is designed for a specific extraction characteristic. Based on the difference in cleanliness desired for the extraction and the difference in the residual liquid, the number of times of the pipetting and injection may be increased or reduced. The injection of other reaction liquid compositions desired for subsequent testing may even be added the last time. All of these are possible modifications.

During the elution step, a nucleic acid addition unit 7 may be needed, which may be used for pipetting the eluent from the kits 5 in the reagent region and injecting it into the cuvette 18a. The nucleic acid addition unit 7 may include a nucleic acid holding arm (not shown), which may achieve the operation of pipetting the eluent from the kits 5 through the reagent pipetting tip and injecting it into the reaction vessels. The elution mechanism may perform the elution process and extract the elution products obtained by the elution to the elution product storage region. For example, in the case that the elution product is the nucleic acid, the nucleic acid may be extracted to the nucleic acid storage region 6a. In this case, an elution grasper 10, an elution plate 9 and a nucleic acid mixer 8 may be provided. The elution grasper 10 may pick up the reaction vessels from the separation mechanism to the elution plate 9, or pick up the reaction vessels from the elution plate 9 to the nucleic acid mixer 8. The elution plate 9 may achieve the elution and incubation operations to the fluid in the reaction vessels. The nucleic acid mixer 8 may achieve the mixing operation to the fluid in the reaction vessels.

Figure 4:
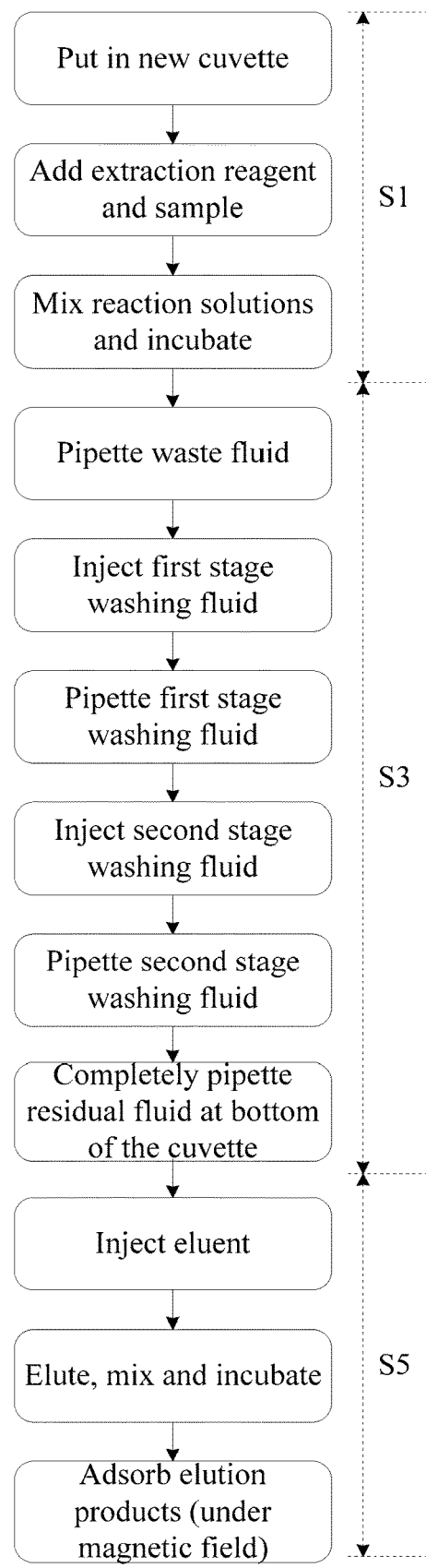
FIG. 4 is a schematic flow chart of the operation of the nucleic acid extraction apparatus according to an embodiment of the present disclosure.

A process of achieving one nucleic acid extraction using the nucleic acid extraction apparatus according to an embodiment of the present disclosure will be provided below with reference to FIG. 1 and FIG. 4. The process may include three steps: a loading and incubation step S1, a magnetic separation and purification step S3 and an elution step S5. The process of achieving this one nucleic acid extraction may be completed in one cuvette 18a, which may be a disposable consumable. There may also be one circulation tube 18b cooperatively used with the cuvette 18a. The circulation tube 18b may be used for carrying the waste fluid generated during the magnetic separation process and the sample pipetting tip 18c used in the pipetting for the magnetic separation.

In the loading and incubation step S1, the cuvette 18a, the circulation tube 18b, and the sample tip 18c located in the circulation tube 18b may be placed on the consumables loading region 1. The consumables grasper 2a may grasp the cuvette 18a and the circulation tube 18b to the incubation plate 13, and then the sample addition unit 2b may, after loading the sample tip 18c, pipette the sample and inject it into the cuvette 18a. Then, the sample tip 18c may be unloaded to the circulation tube 18b. Thereafter, the incubation grasper 14 may grasp the cuvette 18a from the incubation plate 13 to the incubation mixer 15 to perform the mixing. During the mixing, the consumables grasper 2a may again grasp the next cuvette and circulation tube corresponding thereto to the incubation plate 13, and then the same operations described above may be performed. After the incubation mixing is completed, the cuvette 18a may be grasped back to the incubation plate 13 and incubated for a certain time at a constant temperature. After the incubation of the cuvette 18a begins, the next cuvette may be grasped by the incubation grasper 14 from the incubation plate 13 to the incubation mixer 15 where the mixing may be performed.

In the magnetic separation and purification step S3, the cuvette 18a in which the incubation is completed and the circulation tube 18b (in which the sample tip 18c is located) corresponding thereto may be again grasped by the incubation grasper 14 from the incubation plate 13 to the magnetic separation plate 12. The magnetic field may be arranged outside of the magnetic separation plate 12, and the magnetic adsorption may be achieved to the cuvette 18a under the action of the magnetic field. The cuvette 18a may be rotated clockwise at a fixed time interval. When the cuvette 18a and the circulation tube 18b are rotated to the position of the pipetting mechanism 16a, the pipetting mechanism 16a may load the sample tip 18c and then pipette the waste fluid in the cuvette 18a. Then, the waste fluid may be discharged to the circulation tube 18b, and the sample tip 18c may be unloaded to the circulation tube 18b, and at the same time, the elution grasper 10 may grasp the cuvette 18a for which the magnetic separation is completed from the magnetic separation plate to the elution plate, or the incubation grasper 14 may grasp the next cuvette from the incubation plate 13 to the magnetic separation plate. When the cuvette 18a for which the pipetting is completed continues to be moved forward and gets to the position below the pipetting mechanism 16a, the injection mechanism 17a may inject the washing fluid. Then, the cuvette 18a may be backed to the position below the pipetting mechanism 16a, and the pipetting mechanism 16a may load the sample tip 18c and perform suction mixing to the fluid in the cuvette 18a. At this point, the first stage magnetic separation operation is completed. The cuvette 18a and the circulation tube 18b thereof may continue to be moved forward clockwise and successively enter into the positions below the pipetting mechanism 16b, the injection mechanism 17b and the pipetting mechanism 16b of the next stage to complete the magnetic separation operation of the second stage. When the magnetic separation operation of the second stage is performed on the cuvette 18a, the magnetic separation operation of the first stage may be performed on the next cuvette. Thereafter, the cuvette 18a and the circulation tube 18b thereof may continue to be moved forward to get to the positions below 16c and 16d to perform the separation operations of the third stage and the fourth stage. However, different from the magnetic separation of the previous two stages, only the pipetting operation may be performed in the magnetic separation of the latter two stages, but new washing fluid may not be injected.

In the elution step S5, the cuvette 18a for which the magnetic separation is completed may be grasped by the elution grasper 10 from the magnetic separation plate 12 to the elution plate 9 where the elution operation may be performed, and the corresponding circulation tube 18b and the sample tip 18c may be grasped by the elution grasper 10 and discarded at the discarding position 11b. The nucleic acid addition unit 7 may pipette the eluent from the kits 5 and inject it into the cuvette 18a. Then, the elution grasper 10 may grasp the cuvette 18a to the nucleic acid mixer 8, and then grasp it back to the elution plate 9 after the mixing operation is completed. The cuvette 18a may begin the constant temperature incubation in the elution plate 9, and at the same time the nucleic acid grasper 10 may grasp the next cuvette to the nucleic acid mixer 8, where the mixing operation may be completed. The elution may be completed after the constant temperature incubation of the cuvette 18a has been performed for a certain time. The nucleic acid addition unit 7 may, after loading the nucleic acid tip 6*b* from the nucleic acid tip kit 6*c*, pipette the elution products from the cuvette 18*a* and inject them into the wells on the nucleic acid output plate 6*a*, where the step of pipetting the elution products may be completed under the action of the magnetic field in order to prevent the magnetic beads from being adsorbed. Thereafter, the nucleic acid tip 6*b* may be unloaded to, and discarded at, the discarding position 11*b*. Finally, the cuvette 18*a* for which the testing is completed may be grasped by the nucleic acid grasper 10 and discarded at the discarding position 11*b*. At this point, the testing is completed.

In various embodiments, in order to solve the cross contamination problem existing in the plate-type scheme, fully automated nucleic acid extraction apparatuses based on using cuvettes and the operation methods thereof are disclosed. In such apparatuses, each testing may be completed in a single disposable reaction vessel. Each testing may involve a plurality of testing steps, including injection of reaction fluid, mixing and incubation, magnetic separation and elution, etc., and in each testing step a single reaction vessel may be used as the processing unit. For example, after the reaction vessel A1 completes the operation B1, it may be transported to next operation B2 to perform the operation B2, and at the same time next reaction vessel A2 of the reaction vessel A1 may be transported to the operation B1 to perform the operation B1, and so on. Therefore, a single reaction vessel may be transported and used as the processing unit, and it will be unnecessary to perform the same operation on a plurality of samples in parallel. The distance between the tests may be effectively increased, the parallel operations between different tests may be reduced, and thereby the cross contamination problem between the tests may be effectively solved.

The present disclosure has been described with reference to specific examples, which are merely used to facilitate the understanding of, but not to limit, the invention. For a person ordinarily skilled in the art, modifications to the specific embodiments described above may be made according to the concepts disclosed above.

We claim:

1. A nucleic acid extraction apparatus, comprising: at least one cyclically moveable annular structure, wherein the annular structure is provided with a plurality of cuvette positions which are arranged at intervals and used for carrying reaction vessels, and the annular structure is provided, along a cyclical movement path thereof, with at least one operation position used for performing a pipetting operation and at least one operation position used for performing an injection operation;

at least one pipetting mechanism performing the pipetting operation and arranged along the annular structure;

at least one injection mechanism performing the injection operation and arranged along the annular structure; and a driving mechanism driving the annular structure to move cyclically, wherein three annular structures respectively act as an incubation mechanism providing an incubation place for reaction solutions, a separation mechanism for separating a nucleic acid-binding carrier adsorbed with nucleic acid from the reaction solutions, and an elution mechanism forming elution products by adding eluent, wherein the separation mechanism is provided with an adsorption mechanism which provides a desired adsorption force for the reaction vessels located at predetermined positions on the separation mechanism.

2. The nucleic acid extraction apparatus of claim 1, wherein the separation mechanism and the incubation mechanism are respectively further provided, along an annulus thereof, with a plurality of circulation tube positions which are used for carrying circulation tubes receiving waste fluid, and each of the circulation tube positions is adjacent to a cuvette position corresponding thereto.

3. The nucleic acid extraction apparatus of claim 1, wherein the pipetting operation is performed by the at least one pipetting mechanism using disposable pipetting tips.

4. The nucleic acid extraction apparatus of claim 1, further comprising at least one transport mechanism transporting the reaction vessels in and out of the annular structures.

5. The nucleic acid extraction apparatus of claim 1, further comprising at least one mixer mixing reaction solutions in the reaction vessels.

6. The nucleic acid extraction apparatus of claim 1, wherein the at least one injection mechanism at least injects nucleic acid-binding carrier and washing fluid into the reaction vessels located on at least one of the annular structures.

7. A nucleic acid extraction apparatus, comprising: an incubation mechanism providing an incubation place for reaction solutions;

a separation mechanism separating a nucleic acid-binding carrier adsorbed with nucleic acid from the reaction solutions, wherein the separation mechanism is a cyclically moveable annular structure and is provided, along an annulus thereof and at intervals, with a plurality of cuvette positions which are arranged in at least one column and used for carrying reaction vessels, and wherein the separation mechanism is provided, along a cyclical movement path thereof, with an in/out position used for taking the reaction vessels out of the separation mechanism or inserting the reaction vessels into the separation mechanism, at least one pipetting position and at least one injection position;

at least one pipetting mechanism performing a pipetting operation at the at least one pipetting position of the separation mechanism;

at least one injection mechanism performing an injection operation at the at least one injection position of the separation mechanism; and at least one transport mechanism transporting the reaction vessels in and out of the incubation mechanism and the separation mechanism;

wherein the incubation mechanism is a cyclically moveable annular structure, and the incubation mechanism is provided, along an annulus thereof and at intervals, with a plurality of cuvette positions which are arranged in at least one column and used for carrying the reaction vessels;

wherein the separation mechanism and the incubation mechanism are respectively further provided, along annuluses thereof, with a plurality of circulation tube positions which are used for carrying circulation tubes receiving waste fluid, and each of the circulation tube positions is adjacent to a cuvette position corresponding thereto.

8. The nucleic acid extraction apparatus of claim 7, wherein the separation mechanism is cyclically stepped at a predetermined rotation step length and in a predetermined rotation direction and performs a predetermined operation during a stop period, and wherein, during the stop period of the separation mechanism for performing operations, the transport mechanism picks up the reaction vessels in which the incubation is completed from the incubation mechanism to the in/out position of the separation mechanism, or picks up the reaction vessels in which the separation is completed and which are located on the in/out position of the separation mechanism.

9. The nucleic acid extraction apparatus of claim 7, wherein, during a stop period of the transporting of the reaction vessels by the transport mechanism, the transport mechanism further transports the circulation tubes following the reaction vessels.

10. The nucleic acid extraction apparatus of claim 7, wherein the nucleic acid extraction apparatus further comprises an incubation mixer, wherein the at least one injection mechanism comprises a sample addition mechanism and a reagent addition mechanism, and wherein: the incubation mechanism is provided, along a cyclical movement path thereof, with mixing positions used for taking the reaction vessels out of the incubation mechanism to perform mixing, insertion positions used for inserting the reaction vessels in the incubation mechanism, sample addition positions and reagent addition positions;
the incubation mechanism is cyclically stepped at a predetermined rotation step length and in a predetermined rotation direction;
during a stop period of the incubation mechanism for performing operations, the at least one transport mechanism picks up the reaction vessels located on the mixing positions of the incubation mechanism to the incubation mixer, or picks up the reaction vessels in the incubation mixer in which the mixing is completed to the mixing positions;
the at least one transport mechanism picks up empty reaction vessels to the insertion positions of the incubation mechanism;
the sample addition mechanism adds sample into the reaction vessels located on the sample addition positions of the incubation mechanism; and
the reagent addition mechanism adds reagent into the reaction vessels located on the reagent addition positions of the incubation mechanism.

11. The nucleic acid extraction apparatus of claim 10, further comprising a nucleic acid mixer and an elution mechanism forming elution products by adding eluent, wherein: the injection mechanism comprises an eluent addition mechanism, and the elution mechanism is a cyclically moveable annular structure;
the elution mechanism is provided, along an annulus thereof and at intervals, with a plurality of cuvette positions which are arranged in at least one column and used for carrying the reaction vessels;
the elution mechanism is provided, along a cyclical movement path thereof, with mixing positions, insertion positions used for inserting the reaction vessels in the elution mechanism, and eluent addition positions;
the elution mechanism is cyclically stepped at a predetermined rotation step length and in a predetermined rotation direction;
during a stop period of the elution mechanism for performing operations, the transport mechanism picks up the reaction vessels located on the mixing positions of the elution mechanism to the nucleic acid mixer, or picks up the reaction vessels in the nucleic acid mixer in which the mixing is completed to the mixing positions; and
the eluent addition mechanism adds eluent into the reaction vessels located on the eluent addition positions of the elution mechanism.

12. The nucleic acid extraction apparatus of claim 7, wherein the nucleic acid extraction apparatus further comprises an adsorption mechanism providing a desired adsorption force for the reaction vessels located on predetermined positions of the separation mechanism.

13. An operation method of a nucleic acid extraction apparatus, wherein the nucleic acid extraction apparatus comprises at least one cyclically moveable annular structure, at least one pipetting mechanism, at least one injection mechanism and a driving mechanism, and the method comprises: the driving mechanism driving the annular structure to cause reaction vessels to cyclically step at a predetermined rotation step length and in a predetermined rotation direction, and a predetermined operation being performed during a stop period;
when the annular structure stops for performing operations, the at least one pipetting mechanism and the at least one injection mechanism performing predetermined operations on the reaction vessels located on operation positions; and
when the predetermined operations are completed, the reaction vessels continuing to be transported to a next operation position within the annular structure;
wherein circulation tube positions used for carrying circulation tubes receiving waste fluid are arranged beside cuvette positions of the reaction vessels in which the waste fluid needs to be discharged, and, before the nucleic acid extraction apparatus performs an elution operation, during a stop period of transport of the reaction vessels by a transport mechanism, the transport mechanism further transports the circulation tubes used for carrying the waste fluid and following the reaction vessels.

14. The method of claim 13, wherein each circulation tube is further used for carrying a disposable pipetting tip, and the pipetting mechanism loads a disposable pipetting tip in a circulation tube before a pipetting operation, performs the pipetting operation through the disposable pipetting tip, and unloads the disposable pipetting tip to the circulation tube after the pipetting operation is completed.

15. An operation method of a nucleic acid extraction apparatus, wherein the nucleic acid extraction apparatus comprises an incubation mechanism, a separation mechanism, at least one pipetting mechanism, at least one injection mechanism and at least one transport mechanism, and the method comprises: driving the separation mechanism to cyclically step at a predetermined rotation step length and in a predetermined rotation direction, and performing a predetermined operation during a stop period; and
when the separation mechanism stops for performing operations, the transport mechanism picking up reaction vessels on which incubation is completed from the incubation mechanism to an in/out position of the separation mechanism, or picking up the reaction vessels on which separation is completed and which are located on the in/out position of the separation mechanism;
wherein, during a stop period of the separation mechanism for performing operations, the at least one pipetting mechanism and the at least one injection mechanism perform predetermined operations on the reaction vessels stopping at pipetting positions and injection positions, respectively;
wherein, during a stop period of transport of the reaction vessels by the transport mechanism, the transport mechanism further transports circulation tubes following the reaction vessels, and each circulation tube is used for receiving waste fluid and carrying a disposable pipetting tip of the reaction vessel which each circulation tube follows.

16. The method of claim 15, wherein the incubation mechanism is a cyclically moveable annular structure, and the method further comprises: driving the incubation mechanism to cyclically step at a predetermined rotation step length and in a predetermined rotation direction;

when the incubation mechanism stops for performing operations, the transport mechanism picking up the reaction vessels located on mixing positions of the incubation mechanism to an incubation mixer, or picking up the reaction vessels in the incubation mixer in which a mixing is completed to the mixing positions;

the transport mechanism picking up empty reaction vessels from insertion positions of the incubation mechanism;

a sample addition mechanism adding sample into the reaction vessels located on sample addition positions of the incubation mechanism; and a reagent addition mechanism adding reagent into the reaction vessels located on reagent addition positions of the incubation mechanism.

17. The method of claim 16, wherein the sample addition mechanism adding the sample into the reaction vessels located on the sample addition positions of the incubation mechanism comprises: the sample addition mechanism loading disposable pipetting tips;

pipetting the sample and adding the sample into the reaction vessels located on the sample addition positions of the incubation mechanism through the disposable pipetting tips; and the sample addition mechanism unloading the disposable pipetting tips to the circulation tubes following the reaction vessels.

18. The method of claim 15, wherein in each operation cycle, during which one of the reaction vessels is inserted into the separation mechanism and performed a separation operation, performing at least one pipetting and injection operation and at least one pipetting operation, which operations are performed sequentially, and the pipetting and injection operation comprises: driving the separation mechanism to cause the reaction vessel and the circulation tube thereof to rotate to one of the pipetting positions;

the pipetting mechanism loading a disposable pipetting tip from the circulation tube;

pipetting waste fluid in the reaction vessel through the disposable pipetting tip;

discharging the waste fluid into the circulation tube and unloading the disposable pipetting tip into the circulation tube;

driving the separation mechanism to cause the reaction vessel in which the pipetting is completed and the circulation tube thereof to progress to one of the injection positions;

one of the at least one injection mechanism injecting washing fluid into the reaction vessel;

driving the separation mechanism to bring the reaction vessel in which the injecting is completed and the circulation tube thereof back to the one of the pipetting positions;

one of the at least one pipetting mechanism loading the disposable pipetting tip from the circulation tube; and performing suction mixing to fluid in the reaction vessel through the disposable pipetting tip; and the pipetting operation comprises:

driving the separation mechanism to cause the reaction vessel and the circulation tube thereof to progress to the one of the pipetting positions;

one of the at least one pipetting mechanism loading the disposable pipetting tip from the circulation tube;

pipetting waste fluid in the reaction vessel through the disposable pipetting tip; and discharging the waste fluid into the circulation tube and unloading the disposable pipetting tip into the circulation tube.

* * * * *